United States Patent [19]

Andrews, Jr. et al.

[11] Patent Number: 4,938,847
[45] Date of Patent: Jul. 3, 1990

[54] METHOD OF MANUFACTURING SEMICONDUCTOR DEVICES, INVOLVING THE DETECTION OF WATER

[75] Inventors: John M. Andrews, Jr., Watchung; Nadia Lifshitz, Bridgewater; Gerald Smolinsky, Madison, all of N.J.

[73] Assignee: American Telephone and Telegraph Company, New York, N.Y.

[21] Appl. No.: 395,929

[22] Filed: Aug. 18, 1989

[51] Int. Cl.⁵ .............................................. G01N 27/00
[52] U.S. Cl. .................................. 204/153.22; 357/25; 437/8
[58] Field of Search .............. 204/1 W; 437/8; 357/25

[56] References Cited

FOREIGN PATENT DOCUMENTS 188943 8/1986 Japan .

OTHER PUBLICATIONS

M, Kuhn and D. J. Silversmith, "Ionic Contamination and Transport of Mobile Ions in MOS Structures", J. Electrochem. Soc.: Solid State Science, vol. 118, No. 6, Jun. 1971.

N. J. Chou, "Application of Triangular Voltage Sweep Method to Mobile Charge Studies in MOS Structures", J. Electrochem. Soc.: Solid State Science, vol. 118, No. 4, Apr. 1971.

S. R. Hofstein, IEEE Trans. on Electron Devices, ED-13, 222 (1986).

Primary Examiner—G. L. Kaplan
Attorney, Agent, or Firm—Martin I. Finston

[57] ABSTRACT

Disclosed is a method of semiconductor device fabrication involving the detection of water in a dielectric layer that is part of the body of such device. At relatively high values of a voltage applied across the dielectric layer, water that is present in the dielectric decomposes and releases protons. Varying the applied voltage gives rise to a displacement current. The released protons contribute an ionic component to the displacement current. The ionic component is detected.

18 Claims, 2 Drawing Sheets

METHOD OF MANUFACTURING SEMICONDUCTOR DEVICES, INVOLVING THE DETECTION OF WATER

BACKGROUND OF THE INVENTION

This invention relates to methods of manufacturing semiconductor electronic devices, and more particularly to devices, such as multilevel MOS integrated circuits (ICs), incorporating layers of dielectric material and also incorporating, at more than one level, layers of metal.

The oxide layer of an MOS structure must be of relatively high purity. Mobile ions, for example sodium ions, are known to occur in silicon dioxide layers formed by conventional methods. These ions are detrimental to the performance of MOS devices. In silicon field-effect transistors, for example, mobile ions in the gate oxide layer cause shifts in the operating voltage of the device. One conventional, non-destructive method that has been developed for measuring the mobile-ion concentration in silicon dioxide layers is the Triangular-Voltage-Sweep (TVS) method.

Typically, the TVS method is applied to selected test portions of a wafer to be processed. Each of the test portions is configured as an MOS capacitor, having a silicon substrate, a dielectric layer, typically of silicon dioxide, in contact with the substrate, and a metal contact, typically an aluminum contact, formed in contact with the dielectric layer on the side opposite to the substrate. Significantly, two interfaces are defined by these three layers: an interface between the silicon substrate and the dielectric layer, and a second interface between the dielectric layer and the metal contact.

The TVS method is described, for example, in M. Kuhn and D. J. Silversmith, "Ionic Contamination and Transport of Mobile Ions in MOS Structures," *J. Electrochem. Soc.* Vol. 118,966(1971) and in N. J. Chou, "Application of Triangular Voltage Sweep Method to Mobile Charge Studies in MOS Structures," *J. Electrochem. Soc.* Vol. 118,601(1971). Briefly, during testing of an MOS capacitor, the capacitor is maintained at an elevated temperature, typically 100°-400° C., while a triangular voltage sweep is applied across the capacitor. That is, the applied voltage is varied linearly with time from a negative extreme of, for example, $-10$ V to an equal but opposite positive extreme of, for example, 10 V, and then returned to the initial voltage in the same manner. The sweep rate is relatively slow, typically about 5-100 mV per second. (For present purposes, the applied voltage is negative if the silicon substrate is negative relative to the dielectric layer.) As the applied voltage is varied, the displacement current, that is, the time rate of change of the charge induced at the silicon-dielectric interface by the applied voltage, is continuously monitored. The displacement current has, in addition to an electronic component, a component due to the motion of mobile ionic impurities, for example, sodium ions. A graph, here called a characteristic curve, is readily constructed in which the vertical axis represents the displacement current and the horizontal axis represents the sweep voltage (or sweep time, which is typically proportional to the sweep voltage). In many dielectrics, the ionic component due to alkali-metal ions appears in the characteristic curve as a well-defined peak appearing near mid-sweep, that is, near zero applied volts. The area under the peak is proportional to the concentration of mobile ionic impurities.

Additionally, if defects or a conduction path are present in the dielectric, a leakage current may appear. The presence of a leakage current causes the characteristic curve to have a non-zero slope. However, this effect is readily prevented by growing a blocking layer of a highly insulating dielectric, such as high-quality thermally grown silicon dioxide, between the silicon substrate and the dielectric layer to be tested.

In addition to ionic impurities such as sodium, another undesirable impurity in MOS structures is water. Water is an undesirable contaminant in MOS integrated circuits because it can engender protons that may degrade the threshold voltage and transconductance of MOS transistors. In addition, contamination by water is undesirable whenever an aluminum contact is to be deposited in a window etched through the dielectric. Water that is outgassed by the dielectric while the aluminum is being deposited can oxidize the aluminum at the point of contact, thus raising the contact resistance to an unacceptable level.

Contamination by water is a particularly significant problem in low-temperature dielectrics such as spin-on silicon dioxides, which are of interest for forming intermediate dielectrics in vertically integrated VLSI structures. Low-temperature dielectrics are desirable because, for example, they can be deposited at temperatures low enough to avoid diffusion of the aluminum of a first-level metallization layer and formation of aluminum filaments, which could penetrate a shallow p-n junction. However, these materials have relatively low densities (compared, for example, to thermal oxide), and they readily absorb atmospheric moisture.

Thus, a method is needed for fabricating semiconductor devices that includes the step of detecting water in dielectric layers in order to determine whether the water content is within acceptable limits. Until now, however, there has been no non-destructive, wafer-level technique for detecting water in dielectric layers.

SUMMARY OF THE INVENTION

We have discovered that when an electric field of sufficient intensity is created in a water-containing dielectric layer by applying a voltage of sufficient amplitude across the layer, and the layer is simultaneously maintained at an elevated temperature, some of the water decomposes to produce mobile protons. The induced motion of these protons is readily detected as electric current or as induced electric charge. The induced current or induced charge is indicative of the degree of water contamination.

Thus, we are here disclosing a method for fabricating a semiconductor device that includes the step of detecting the water in a dielectric layer by heating the layer and applying an electric field sufficiently intense to decompose some of the water, resulting in the production of mobile charge in the form of protons. In one embodiment of the invention, the protons are detected by observing the current induced by a constant applied voltage. In another embodiment, the protons are detected by observing a TVS characteristic current curve. In yet another embodiment, a modified TVS technique is used. The TVS technique and the modified TVS technique both comprise the steps of forming an MOS capacitor structure including a dielectric on a wafer, heating the wafer, and applying a changing (e.g., linearly changing) voltage across the dielectric. However, unlike the TVS technique, the modified TVS technique further comprises the steps of varying the voltage in discrete increments, and monitoring the change in induced charge in response to each voltage increment, in order to detect behavior indicative of the presence of water. The behavior sought may appear as one or more features of the characteristic curve.

As noted, the peak applied voltage must be great enough to dissociate water that is present in the dielectric layer. For purposes of both the TVS technique and the modified TVS technique, the peak applied voltage is, for example, selected to produce in the dielectric an average electric field greater than about 1 MV/cm. In connection with both TVS and modified TVS, the range over which the applied voltage is varied is here called the voltage sweep, even though in modified TVS the voltage is not swept continuously, but rather is varied in discrete increments.

DETAILED DESCRIPTION

In a broad sense, the invention is a method of semiconductor device fabrication including the step of detecting water in a dielectric layer which is a part of the body of such device, wherein the detecting step comprises heating the body to an elevated temperature, applying across the dielectric layer a voltage sufficient to decompose water, whereby protons are generated, and electrically detecting the protons.

For example, as noted above, water absorbed in a dielectric layer decomposes to release protons both at the endpoints of a TVS, or modified TVS, voltage sweep, where the voltage is at its positive or negative peak value, and also during at least part of the voltage sweep between the endpoints. The protons are generated at random locations within the bulk of the dielectric and migrate toward whichever interface has negative polarity at that moment. In particular, protons are generated during the time that a relatively high electric field is being applied to the dielectric near the beginning and end of the forward voltage sweep and near the beginning and end of the reverse voltage sweep. The resulting proton current is readily detected as part of the displacement current. As the applied voltage is swept toward zero, the proton generation rate falls off. As a consequence, the proton current also falls off, but the proton generation rate and the proton current increase again after the applied voltage passes zero and approaches the opposite holding voltage.

Figure 1:
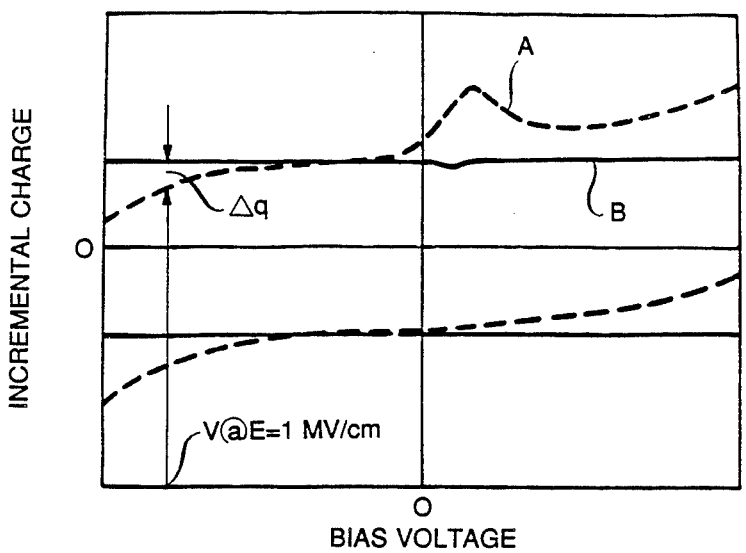
FIG. 1 is an idealized representation of typical characteristic curves. Shown is Curve A, corresponding to a dielectric containing water-related charge, and Curve B, corresponding to a dielectric containing no mobile charge.

As a result of proton generation, the characteristic curve has a non-zero slope throughout the entire sweep cycle, the effect being particularly pronounced near the end points of the voltage sweep. This behavior is depicted in FIG. 1, where Curve A, an idealized representation of a characteristic curve of a dielectric containing water-related charge, is shown deviating from Curve B, which represents a dielectric containing no mobile charge. As is apparent from Curve B, in the absence of mobile charge the characteristic curve is flat near the endpoints (assuming there is no leakage current). Conversely, the existence of a non-zero slope in the characteristic curve is evidence that mobile charge is present in the dielectric (again assuming there is no leakage current). Such a non-zero slope may be dependent upon voltage; that is, the characteristic curve may exhibit steeper slope near the endpoints.

The bending of the characteristic curve of a dielectric containing water may resemble the bending caused by a leakage current. However, the water-related bending is observed even when leakage current is prevented by a blocking layer of thermal silicon dioxide. Mobile ionic impurities, such as sodium ions, that do not change in number during the application of the voltage sweep do not cause the characteristic curve to deviate from zero slope.

In addition, the MOS capacitor is readily stressed at the endpoints of the voltage sweep by holding it for a chosen period, for example about two minutes, at the positive or negative peak voltage. During this holding period, positive mobile charge in the dielectric accumulates at the interface having negative polarity. If, initially, the silicon/dielectric interface is the negative interface (i.e., the initial holding voltage is negative), then subsequently, somewhere in the middle of the sweep from the negative holding voltage toward the positive holding voltage, the protons that have accumulated within the dielectric at the silicon/dielectric interface begin to move to the opposite interface. In many dielectrics, this motion is coherent and causes a peak to appear in the characteristic curve near zero applied volts, that is, near where the applied voltage crosses over from negative to positive values. However, this peak is not symmetric. That is, it is absent from the reverse trace. By contrast, the peaks corresponding to coherent motion of ionic impurities such as sodium, are fully symmetric. We attribute the absence of a proton peak during the reverse sweep to the trapping of protons at the dielectric/aluminum interface as described, for example, in S. R. Hofstein, *IEEE Trans. on Electron Devices*, ED-13, 222 (1966). Apparent in Curve A of FIG. 1 is a mobile proton peak in the positive-going portion of the voltage sweep.

It is to be noted that in some dielectrics, the dissociation of the protons from the silicon/dielectric interface and their subsequent motion through the dielectric may not be coherent. Accordingly, the TVS characteristic curve of these materials may not exhibit a well-defined peak. As a consequence, the bending of the TVS characteristic curve, rather than the mobile charge peak, is a more generally applicable indicator of the presence of mobile protons in the dielectric.

As a pedagogical aid to a more complete understanding of the invention, a particular embodiment, involving the modified TVS method, is described below. The MOS capacitor is first heated to an elevated temperature of at least about 100° C., but not more than about 400° C., and typically about 300° C. During the entire process, the capacitor is maintained constantly at the elevated temperature.

If the MOS capacitor is to be stressed, then prior to the voltage sweep it is subjected to a negative holding voltage greater than, or, preferably, equal to, the peak sweep voltage. Typically, a symmetric sweep is used, and the holding voltage typically equals the peak sweep voltage. The peak voltages are chosen to subject the dielectric to an average electric field of at least about 1 MV/cm. A typical sample has a composite dielectric structure as depicted, for example, in FIG. 2. Such a structure comprises, for example, a 2000-Å-thick layer 30 of the dielectric to be tested, sandwiched between a layer 20 of thermally grown silicon dioxide 500 Å in thickness, and a capping layer 40 of, for example, PE-PTEOS 1500 Å in thickness. The purpose of the capping layer is to impede the absorption of atmospheric moisture. Thus the total dielectric thickness in a typical sample is about 4000 Å, and the corresponding holding voltage is typically about 50 V.

The capacitor is maintained at the holding voltage for a selected holding period long enough for substantial mobile positive charge in the dielectric to accumulate at the silicon/dielectric interface. This period is typically about two minutes.

The voltage sweep is than applied by increasing the voltage in discrete increments of, for example, about one volt until it reaches the holding voltage of the opposite sign. The charge appearing in the system due to each voltage increment is recorded directly. This is advantageous over conventional TVS because it is independent of any calibration factors. That is, if a linear voltage ramp as in conventional TVS is used, varying the voltage at a continuous rate of $\alpha$ volts per second, then the displacement current that is measured depends both on the rate $\alpha$ and on the proton generation rate.

In modified TVS, by contrast, each time the voltage is stepped by a discrete increment, the differential charge induced by that increment is recorded directly. The recorded result is equal, in an absolute sense, to the total induced charge, independent of the sweep rate. This is true even if significant numbers of protons are generated during the sweep.

Moreover, the sweep rate of a (continuous) linear voltage ramp, as is used in conventional TVS, is limited by the equilibration time of the mobile charge. That is, the voltage must be varied slowly enough to permit continuous equilibration of the mobile charge, and therefore the sweep rate cannot exceed the equilibration rate. By contrast, an incremental sweep can be performed more quickly than a linear voltage ramp. This is because the equilibration time following each voltage increment is not proportional to the size of the voltage increment. Instead, for voltage increments of the order of a few volts or less, the equilibration time is approximately independent of the size of the increment. As a consequence, voltage increments of arbitrary size (up to a few volts) can be repeated at relatively short intervals of, for example, a few tenths of a second. The result is that a complete voltage sweep can be completed in less time if it is performed incrementally rather than continuously.

If an incremental sweep is used, the voltage is maintained at a selected aging time after each increment. The aging time should be sufficient for the equilibration of the mobile charge and the measuring system. However, the mobile charge usually equilibrates within a time period much smaller than the response time of the measuring instruments. As a consequence, this response time, which is typically about 0.3 seconds, is a sufficient aging time. Longer aging times, for example aging times of about two seconds, are possible and have been used in practice.

The displacement charge appearing in the system as a result of each voltage increment is measured and recorded. When the voltage reaches the peak voltage of the opposite sign, the capacitor is again readily stressed so as to accumulate the mobile charge at the aluminum/dielectric interface. The voltage is then incremented in the opposite direction, so that at the end of the cycle the applied voltage returns to its original value.

We have discovered that the slope of the characteristic curve depends on the temperature, the holding voltage, and the aging time (or the sweep rate $\alpha$ in conventional TVS, where the voltage is swept continuously). Because the rate of proton generation increases with voltage, as noted above, the slope may increase in magnitude when the voltage is increased in magnitude. Moreover, at a given voltage sufficient to generate protons, increasing the aging time increases the accumulation of protons and thus increases the proton current contributing to a single incremental measurement. Thus, longer aging times cause greater slope, and, significantly, increase the sensitivity of the modified TVS method.

This characteristic of modified TVS is distinct from conventional TVS, where although decreasing $\alpha$ increases the accumulation of protons by a certain factor, it also decreases the displacement current by approximately the same factor. Thus the two effects substantially cancel, and the sensitivity of conventional TVS to water cannot be substantially improved by decreasing the sweep rate.

The proton generation process has not been observed to saturate because only a small fraction of the total absorbed water is decomposed under typical test conditions.

For making comparisons between different samples, or for comparing the properties of the same sample at different times, it is desirable to examine the difference $\Delta q$ between the incremental displacement charge in the dielectric with that in an uncontaminated dielectric having the same thickness, area, and dielectric constant at a given electric field, for example, 1 MV/cm, and at a specified temperature and aging time, as illustrated in FIG. 1. Thus, for example, when an incremental voltage scan is used at 300° C. with an aging time of two seconds, a useful value for purposes of comparison is the charge generation rate obtained by dividing $\Delta q$ by the product of the dielectric volume times 2 seconds, where $\Delta q$ is evaluated at the point in the voltage sweep where the average field in the dielectric is 1 MV/cm.

Alternatively, if the dielectric is to be stressed prior to the voltage sweep, the presence of generated mobile charge may be qualitatively detected by observing the non-symmetric mobile charge peak. However, as noted, not all dielectrics exhibit this peak.

Figure 3:
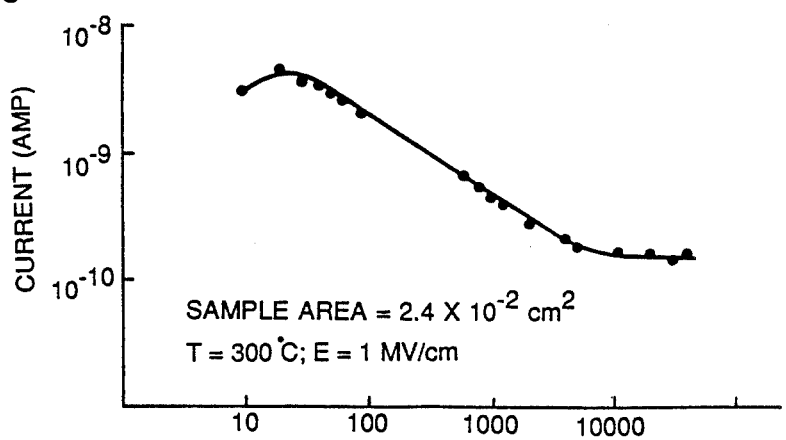
FIG. 3 is a graph of ionic current versus time at a constant applied voltage for a typical MOS capacitor prepared for application of the inventive method.

According to an alternate embodiment of the invention, specific reference values of the average electric field and the temperature are selected, for example, 1 MV/cm and 300° C., respectively, and the displacement current is observed over an extended period of time, for example, several hours to several hundreds of hours. The ionic component (i.e., that portion of the total current due to the migration of protons) is advantageously distinguished from the current component that would obtain in an uncontaminated dielectric. The time integral of the ionic component is equal to the total mobile charge in the sample due to the release of protons by the selected test conditions. The current is advantageously observed, and the integration carried out, until the ionic current decays to the noise level, which is typically a few hundred picoamperes. Significantly, this method permits absolute comparisons between different materials. FIG. 3 shows the time dependence of the ionic current in a typical sample.

By way of example, Table 1 compares seven different dielectric materials (and, in the case of one particular material, PE-PTEOS, compares two different deposition temperatures) subjected to varying times of exposure to the atmosphere. The basis for comparison in the table is the charge-generation rate at the point in the voltage sweep where the average electric field in the dielectric is 1 MV/cm, with the sample maintained at 300° C., and using an incremental voltage sweep with an aging time of two seconds.

EXAMPLE

Figure 2:
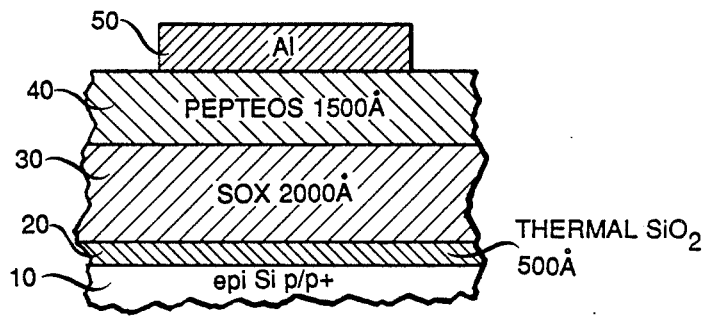
FIG. 2 is a schematic cross-sectional view of a typical MOS structure having composite oxide layers, prepared for application of the inventive method.

MOS capacitors were prepared having a dielectric layer of SOX, a spin-on silicon oxide. As depicted in FIG. 2, each capacitor comprised silicon substrate 10, thermal silicon dioxide layer 20, SOX layer 30, PE-PTEOS layer 40, and aluminum contact 50. It is apparent that this structure is a composite oxide structure, incorporating not only SOX, but also PE-PTEOS and, in a relatively thin layer, thermally grown silicon dioxide. PE-PTEOS is a low-temperature plasma-enhanced, phosphorus-doped, silicon oxide deposited through a process involving tetraethoxysilane chemistry. This material may be doped with phosphorus in concentrations as high as 8%. The material used here was doped to 4%.

Preparation of SOX solution

To prepare a SOX solution, an aliquot of 1-propanol (33.2 g, 41.3 mL) was first added to 20 g of silicon(IV) acetate. Dissolution was achieved after a few minutes of agitation with a magnetic spin bar. The slightly cloudy solution was filtered sequentially through a 10, 5 or 3, and 0.2 $\mu$m filter. Twenty-four hours later, one molar equivalent of water (based on a 4% silicon content) was added to the filtrate. The SOX solution was ready for film deposition 72 hours after dissolution of the acetate in the alcohol and was used within the next 48 hours or discarded.

Fabrication of Samples

MOS capacitors were made by cleaning four-inch-diameter, epitaxial-(p/p+)-<100>-silicon wafers and preparing them for TVS measurements as follows.

First, a 500 Å oxide layer was grown at 1000° C. in HCl and oxygen. The purpose of this oxide layer was to provide a blocking layer of high quality insulator between the silicon substrate and the dielectric layer to be tested, in order to prevent leakage currents.

Second, the wafers were spin-coated with about 2000 Å of SOX at 3500 rpm using a Semiconductor System, Inc., automated spin-coating tool equipped with an in-line, three-hot-plate wafer track. The coated wafers were cured by first hot-plate baking for 4 minutes at 75° C. and 2 minutes at 150° C., and then furnace baking for 2 hours at 400° C. in oxygen. The index of refraction of the cured SOX was 1.42 with a one-coat thickness of about 2050 Å. The density of the material, as determined by the Rutherford back scattering technique, was found to be 70–80% of thermal $SiO_2$.

Third, 1500 Å of PE-PTEOS was deposited at 400° C. in a plasma-enhanced CVD reactor. (Prior to deposition the substrate was held in the pumped-down reactor at 400° C. for 20 minutes. The oxide was deposited at a rate of about 200 Å/minute).

Finally, 1 $\mu$m of aluminum was magnetron sputtered onto the surface of each wafer. The aluminum was patterned into $2.4 \times 10^{-2}$ cm$^2$ electrode dots. The fabricated MOS devices were annealed at 450° C. in hydrogen.

Electrical Measurements

The dielectrics were characterized using a digital system that approximated a triangular-ramp voltage with a stepping-ramp voltage. A Keithley Model 617 programmable electrometer was connected in the coulomb mode in conjunction with a built-in programmable voltage source. The voltage source was connected to the chuck that held the wafer. The device wafer was maintained at a constant elevated temperature with a Thermochuck Model TP36 System manufactured by Temptronic, Incorporated.

First, the MOS capacitor was stressed for two minutes at the negative holding voltage to accumulate all positive mobile charge in the dielectric at the silicon/dielectric interface. The voltage on the capacitor was then incremented in steps of one volt and aged for two seconds after each voltage increment. The coulomb meter was automatically zeroed prior to each voltage increment, and the total displacement charge appearing in the system as a result of each voltage increment was measured and the value stored in a two-dimensional array. Thus the data could be plotted later in the form of the dependence of the incremental charge on the applied voltage.

When the voltage reached the holding voltage of opposite sign, the capacitor was again stressed. During the second part of the test, the bias increments were opposite in sign to those of the first part, and thus at the end of the cycle the bias returned to its original value.

Results

Figure 4:
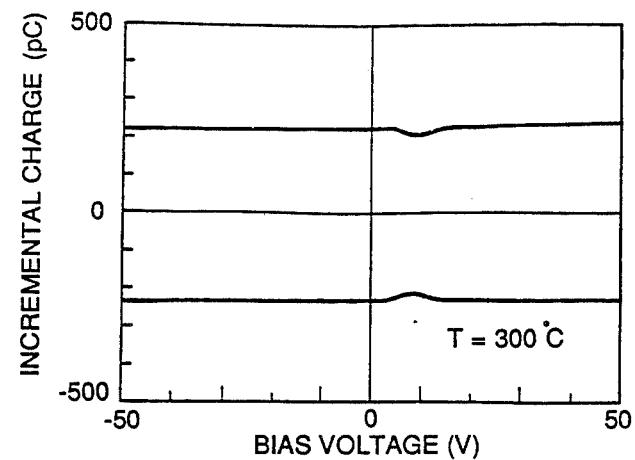
FIG. 4 is a characteristic curve of PE-PTEOS dielectric produced according to the inventive method.
Figure 5:
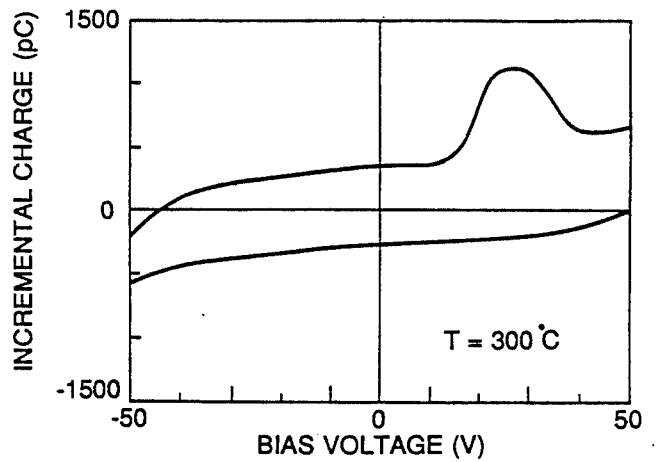
FIG. 5 is a characteristic curve of SOX dielectric produced according to the inventive method.

FIG. 4 depicts a characteristic curve taken on a sample similar to the SOX sample, but having a 3500-Å-thick layer of PE-PTEOS instead of the composite layer of PE-PTEOS and SOX. No slope or mobile-ion peak is observed. FIG. 5 depicts an analogous characteristic curve taken on a sample having a composite layer of PE-PTEOS and SOX. Both a voltage-dependent slope and a mobile-ion peak are observed. (The peak is observed only for the positive-going sweep direction). This curve was taken at 300° C., with stressing at the endpoints, at positive and negative peak voltages of 50 V, respectively.

Figure 6:
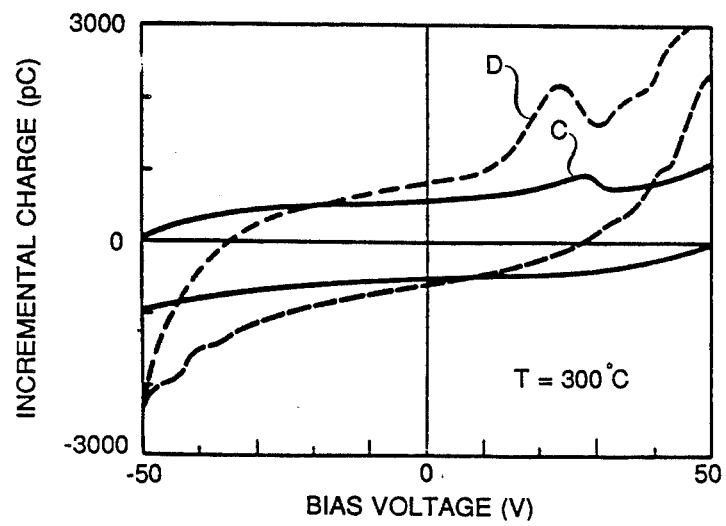
FIG. 6 consists of a pair of characteristic curves of SOX dielectric, illustrating the effect of atmospheric exposure on the appearance of the characteristic curve.

FIG. 6 illustrates the effect of exposure to the atmosphere on the characteristic curve of a SOX sample as described. Curve C was taken immediately after annealing the sample at 450° C. Curve D was taken after several days of exposure to ambient room conditions. It is apparent that both the endpoint curvature and the mobile-charge peak became more pronounced after exposure. Significantly, the characteristic curve was restored to the shape of Curve C by again annealing the sample for several hours at 300° C.

Referring back to FIG. 3, there is shown the time-dependence of the proton current in the SOX sample at 300° C. and an average electric field in the dielectric of 1 MV/cm. The total number density of mobile protons determined by integrating the current-vs.-time curve of this figure was $1.4 \times 10^{19}$ cm$^{-3}$. Significantly, a neutron activation analysis of SOX samples exposed to the atmosphere detected a much higher hydrogen concentration, about $10^{21}$–$10^{22}$ cm$^{-3}$. This indicates that only a small fraction of water-bound hydrogen is activated under the test conditions.

TABLE

The initial proton current at 300° C. and 1 MV/cm, as determined from TVS plots.

| Material | Thickness (A) | Remarks | Δq (pC) | Generation Rate (charge cm$^{-3}$ sec$^{-1}$) |
|---|---|---|---|---|
| PE-PTEOS (Depos. 350° C.) | 3500 | After 450° C. Ann. | 0 | 0 |
|  |  | 6 Mo. Later | 100 | $3.7 \times 10^{14}$ |
| (Depos. 300° C.) |  | After 450° C. Ann. | 30 | $2.2 \times 10^{14}$ |
| Accuglass 211 | 2000, PE-PTEOS | After 450° C. Ann. | 0 | 0 |
|  |  | 1 Week Later | 40 | $2.6 \times 10^{14}$ |
| PLOX | 3500, no PE-PTEOS | After 450° C. Ann. | 0 | 0 |
|  |  | 1 Month Later | 50 | $1.8 \times 10^{14}$ |
| Accuglass 203 | 2000, PE-PTEOS | After 450° C. Ann. | 240 | $1.6 \times 10^{15}$ |
| SiN:F | 3500, no PE-PTEOS | After 450° C. Ann. | 0 | 0 |
|  |  | 2 Weeks Later | 60 | $2.2 \times 10^{14}$ |
| Thermal SiO$_2$ (Wet Grown) | 1000, no PE-PTEOS | After 450° C. Ann. | 0 | 0 |
|  |  | 6 Mo. Later | 30 | $3.9 \times 10^{14}$ |
| SOX | 2000, PE-PTEOS | Varies, Deteriorates Rapidly in the Air | Up to 1200 | Up to $1.6 \times 10^{16}$ |

We claim:

1. A method of semiconductor device fabrication including the step of detecting water in a dielectric layer which is a part of the body of such device, characterized in that the water-detecting step comprises the steps of:
   heating the body to an elevated temperature;
   applying across the dielectric layer a voltage sufficient, during at least a portion of such application, to create in the dielectric layer an electric field intense enough to decompose water, whereby protons are generated; and
   detecting the protons.

2. The method of claim 1, further comprising the step of varying the voltage between a maximum negative amplitude and a maximum positive amplitude.

3. The method of claim 2, wherein the proton-detecting step comprises detecting the current induced by varying the voltage.

4. The method of claim 2, wherein the maximum negative amplitude and the maximum positive amplitude are each adapted to create in the dielectric a volume-averaged electric field greater than about 1 MV/cm.

5. The method of claim 2, wherein the elevated temperature is at least about 100° C., but not more than about 400° C.

6. The method of claim 2, wherein the varying step comprises:
   increasing the voltage from the maximum negative amplitude to the maximum positive amplitude; and
   decreasing the voltage from the maximum positive amplitude to the maximum negative amplitude.

7. The method of claim 6, further comprising:
   before the increasing step, the step of stressing the dielectric layer at a negative voltage, and
   before the decreasing step, the step of stressing the dielectric layer at a positive voltage.

8. The method of claim 2, wherein the voltage-varying step comprises changing the voltage in discrete increments separated by time intervals, and the proton-detecting step comprises recording the charge induced during each of the time intervals.

9. The method of claim 8, wherein the time intervals are at least about 0.1 second, but not more than about 10 seconds.

10. The method of claim 8, wherein the discrete voltage increments are less than or equal to about 0.05 times the sum of the absolute value of the maximum positive voltage amplitude and the absolute value of the maximum negative voltage amplitude.

11. The method of claim 8, wherein the varying step comprises increasing the voltage from the maximum negative amplitude to the maximum positive amplitude, and decreasing the voltage from the maximum positive amplitude to the maximum negative amplitude; the method further comprising:
   before the increasing step, the step of stressing the dielectric layer at a negative voltage; and
   before the decreasing step, the step of stressing the dielectric layer at a positive voltage.

12. The method of claim 11, wherein during the increasing step, and during the decreasing step, the charge increments have a functional dependence upon the voltage, and the method further comprises the step of observing the functional dependences to detect positive slope in at least one range of voltages between the maximum positive and negative amplitudes.

13. The method of claim 12, wherein:
   the maximum negative amplitude and the maximum positive amplitude are each adapted to create in the dielectric a volume-averaged electric field greater than about 1 MV/cm;
   the elevated temperature is at least about 100° C., but not more than about 400° C.; and
   the time intervals are at least about 0.1 second, but not more than about 10 seconds.

14. The method of claim 11, wherein during the increasing step, and during the decreasing step, the charge increments have a functional dependence upon the voltage, and the method further comprises the step of observing to detect a local maximum in the functional dependence corresponding to the increasing step, together with the absence of a corresponding local minimum in the functional dependence corresponding to the decreasing step.

15. The method of claim 14, wherein:
   the maximum negative amplitude and the maximum positive amplitude are each adapted to create in the dielectric a volume-averaged electric field greater than about 1 MV/cm;
   the elevated temperature is at least about 100° C., but not more than about 400° C.; and
   the time intervals are at least about 0.1 second, but not more than about 10 seconds.

16. The method of claim 1, wherein the applied voltage is constant during at least a portion of the voltage-applying step, such that during the constant-voltage portion, a displacement current having an ionic component is induced; and the method further comprises the steps of:

detecting the ionic component, and integrating the ionic component with respect to time.

17. The method of claim 16, wherein:

the applied voltage during the constant-voltage portion is adapted to create in the dielectric a volume-averaged electric field greater than about 1 MV/cm; and the elevated temperature is at least about 100° C., but not more than about 400° C.

18. The method of claim 17, further comprising, before the constant-voltage portion of the voltage-applying step, the step of stressing the dielectric layer.

* * * * *